United States Patent [19]

Dermarderosian

[11] 4,314,474
[45] Feb. 9, 1982

[54] CRACK DETECTION BY VAPOR CONDENSATION

[75] Inventor: Aaron Dermarderosian, Marlboro, Mass.

[73] Assignee: The United States of America as represented by the Secretary of the Navy, Washington, D.C.

[21] Appl. No.: 116,516

[22] Filed: Jan. 29, 1980

[51] Int. Cl.$^3$ .................. G01N 25/72; G01N 31/02; G01N 21/88
[52] U.S. Cl. ................................. 73/15 FD; 73/104
[58] Field of Search ............................. 73/15 FD, 104

[56] References Cited

U.S. PATENT DOCUMENTS

| | | | |
|---|---|---|---|
| 3,580,066 | 5/1971 | Pliskin et al. | 73/104 |
| 4,215,562 | 8/1980 | Gavrilin et al. | 73/15 FD |

OTHER PUBLICATIONS

"Symposium on Nondestructive Tests in the Field of Nuclear Energy", Apr. 1957, Chicago, Ill., Article by McLain.

*Primary Examiner*—James J. Gill
*Attorney, Agent, or Firm*—R. F. Beers; Prithvi C. Lall; A. P. Durigon

[57] ABSTRACT

A novel method for nondestructively indicating the existence of micron-sized cracks, fissures, and other such faults on the surfaces of integrated circuit semiconductor packages and other test surfaces. An indicating layer of substantially uniform thickness is formed over the entire test surface by directing an inert fluorocarbon vapor into contact with the test surface. The temperature of the test surface is below the dew point of the inert vapor so that the indicating layer forms by condensation. The existence of cracks, fissures, and other such faults is clearly indicated to the unaided eye in a dull outline conforming to the shape of the fault as a result of the differential reflection of incident light off of the indicating condensate-layer. Faulted regions absorb comparatively more light than unfaulted regions.

9 Claims, No Drawings

CRACK DETECTION BY VAPOR CONDENSATION

BACKGROUND OF THE INVENTION

This invention relates to material examination techniques and, more particularly, to an inspection process indicating the existence of cracks, fissures and other such faults on solid surfaces.

Integrated circuit semiconductor electronic components are normally encapsulated in a ceramic or other suitable material for preventing electronic component deterioration resulting from, among other factors, dirt, dust, humidity and/or temperature fluctuations. To insure the physical integrity of the encapsulation, it is customary to inspect the components for the purpose of detecting cracks, fissures and other such faults with a view toward separating the defective from the physically sound products.

Various techniques of crack detection are known by those skilled in the art. U.S. Pat. No. 3,904,545 to Molina is exemplary of the class of penetrant-inspection methods which rely on the visibility of a liquid dye that penetrates into the cracks, fissures and other such faults.

U.S. Pat. No. 2,765,652 to Levengood teaches a crack detection method where the test surface is coated with a liquid silvering solution. Here the cracks, fissures and other such faults are indicated because they remain free from any overlaying by the silvering solution.

U.S. Pat. No. 1,640,567 to Firestone is representative of the photoelectric class of fault indicating techniques. Firestone teaches the use of a microscope, a photocell and associated circuitry responsive to the differential reflectivity of the test surface being examined; a fault condition being indicated by the unequal reflection of incident light.

The prior art techniques tend to be slow, invasive, costly and somewhat ineffective. For example, with the use of dye penetrant indicating techniques, difficulties arise in removing the dye penetrants often requiring extensive cleaning procedures. The photoelectric techniques are undesirable, inter alia, since they require the use of relatively elaborate apparatus which is unsuitable for on-the-spot field use.

SUMMARY OF THE INVENTION

The novel method of fault indication by vapor condensation of the present invention solves the problem of indicating micron-sized cracks, fissures and other such faults on test surfaces in a fast, economical, simple yet effective manner which does not require any special cleaning procedures or the need for relatively elaborate apparatus. The method of the present invention forms an indicating layer over the test surface by directing an inert fluorocarbon vapor into contact with the test surface. The temperatures of the inert fluorocarbon vapor and test surfaces are such that the indicating layer forms by condensation. Cracks, fissures, and other such faults are immediately indicated to the unaided eye in a dull outline conforming to the shape of the fault as the result of the differential reflection of incident light off of the indicating condensate layer. Faulted regions absorb comparatively more light than unfaulted regions.

The fluorocarbon vapor, being inert, does not interact with the material of the test surface. The indicating condensate-layer may be removed from the test surface in a number of simple ways including towel drying.

It has been found that the technique of the invention is capable of indicating cracks, fissures and other such faults of micron size in integrated circuit semiconductor packages and other test surfaces.

It is an object of the present invention to provide a material testing method indicating the existence of cracks, fissures, and other such faults on solid surfaces.

It is an object of this invention to provide a simple, yet extremely reliable method of surface fault indication for insuring the physical integrity of protective enclosures.

It is an object of this invention to provide a surface fault screening method which may be readily utilized on a production line or in the field with relatively unskilled personnel.

It is yet another object of this invention to provide a surface fault indicating method which is nondestructive and which does not require dyes or relatively elaborate apparatus.

DESCRIPTION OF THE PREFERRED EMBODIMENT

The concept of the present invention is the recognition that forming an indicating layer over a test surface by condensing an inert vapor onto the test surface readily indicates the existence of cracks, fissures and other such surface voids by reason of the differential reflection of incident light off of the indicating condensate-layer without requiring sophisticated optical technology or specialized and destructive dye-penetrant techniques.

Voided regions of the test surface under examination absorb comparatively more incident light than unfaulted regions. By overlaying the test surface with an indicating condensate-layer according to the novel method of the present invention, the fracture patterns conforming in shape to the surface faults are made manifest to the unaided eye in contrasting dull outline.

The equipment and material requirements necessary to practice the method of the invention are simple, and no special optics or lighting is required.

In the practice of the method of the invention the use of FC-77, a proprietary fluorocarbon available from the 3-M Co., Commercial Chemicals Division, St. Paul, Minn., 55101, has proven effective for forming the indicating condensate-layer on the test surface of integrated circuit semiconductor packages. However, other low surface tension inert vapors may be used as well as the above material. The only requirement being that the surface tension be such that the indicating condensate-layer wets the test surface under examination. Other test surfaces such as glass or steel may also be examined for surface faults.

Any suitable means for directing the inert vapor into contact with the test surface under examination for forming thereon the indicating condensate-layer may be used. In the preferred embodiment, where FC-77 is utilized, the procedure followed starts by placing a preselected quantity of FC-77 fluid, e.g. 500 ml, into an Erlenmeyer flask. Provide the flask with a two hole rubber stopper.

Into one hole place a preselected length of plastic tubing, e.g. 20–26 inches, such that the tubing entering the hole extends into the fluid and curls about the bottom circumference of the flask.

This length of tubing is connected at the outside end to a source of inert gas, such as air or nitrogen; the inside end is sealed shut and the portion of the tube curling about the bottom circumference is provided with a plurality of pin holes, e.g. 50–100, such that the source of inert gas is capable of being gently bubbled through the FC-77 fluid.

Into the other hole place another preselected length of plastic tubing, e.g. 30–36 inches, the inside end extends approximately ¾ inches into the flask. The outside end is unobstructed and may be termed the "vapor" tube.

Place the thus equipped Erlenmeyer flask into contact with a source of heat such as by placing the flask onto a heater plate. Heat the fluid at a preselected temperature, e.g. 200°–210° F., such that the FC-77 fluid gently boils.

After temperature stability, adjust the flow from the source of inert gas such that the FC-77 droplets condense out at the tip of the "vapor" tube at a rate of between 1 to 2 droplets per second. There should be no "spitting" of fluid allowed at the free end of the "vapor" tube.

This setup produces a mild flow of FC-77 vapor which, when condensed onto a glass microscope slide approximately ½ to ¾ inches from the end of the "vapor" tube, forms a substantially uniform, thin and continuous layer of condensate which readily displays light interference fringes. This condition signals proper set-up of the apparatus.

In order to test for the existence of cracks, fissures and other such faults on the surface of an integrated circuit semiconductor device, direct the inert fluorocarbon vapor into contact with the device by holding the free end of the "vapor" tube about ½ to 1 inch away from the test surface such that an indicating layer of uniform thickness forms by condensation on the test surface.

Hold the device at an angle to a light source, the existence of cracks, fissures and other such faults is indicated in dull outline, in the shape of the fault, as the result of the differential reflection of the incident light off of the indicating condensate-layer. Comparatively less light is reflected back from faulted regions.

The process of detection takes between 1–3 seconds per observation.

Occasionally dust or dirt causes interference problems. In such a case, repeat the test until it is obvious whether the device is faulted or not. A microscope may be used to establish confidence in rejects. In the great majority of cases, however, no doubt remains as the faults are very obvious.

This technique indicating the existence of cracks, fissures and other such faults by vapor condensation is capable of indicating micron-sized faults. The method is extremely fast, requiring only 1–3 seconds per observation, requires no dyes or penetrants, no cleanup before or after testing and is nondestructive.

What is claimed is:

1. A method indicating the existence of cracks, fissures and other such faults on a test surface comprising the steps of:
    forming an indicating layer over the entire test surface by directing an inert fluorocarbon vapor into contact with the test surface, the relative temperatures of the inert vapor and the test surface being such that the indicating layer forms by the process of condensation; and
    visually examining said indicating layer at an angle to a light source, the existence of any cracks, fissures and other such faults being indicated in a dull outline conforming to the shape of the fault as a result of the differential reflection of the incident light off of the said indicating layer, faulted regions absorbing comparatively more of said incident light than unfaulted regions.
2. The method of claim 1 wherein said visual examination is performed with the unaided eye.
3. The method of claim 1 wherein said visual examination is performed with the aid of optical amplifiers.
4. The method of claim 1 wherein said test surface is of a semiconductor material encapsulation.
5. The method of claim 1 wherein the faults detectable are of the order of magnitude of a micron in thickness.
6. The method of claim 1 wherein said fluorocarbon vapor is FC-77.
7. A method indicating the existence of cracks, fissures and other such faults on a test surface comprising the steps of:
    forming an indicating layer of an inert fluorocarbon material over the entire test surface, and
    visually examining said indicating layer at an angle to a light source, the existence of any cracks, fissures and other such faults being indicated in a dull outline conforming to the shape of the fault as a result of the differential reflection of the incident light off of the said indicating layer, faulted regions absorbing comparatively more of said incident light than unfaulted regions.
8. In a method for examining solid surfaces so as to determine their integrity and freedom from structural defects, such as cracks and fissures, the steps of:
    forming on said solid surface by a condensation process a covering of an inert fluorocarbon material that has such a relatively low surface tension that the covering material wets the surface, and
    inspecting said covering at an angle to that at which it is being illuminated by a suitable light source, the differential reflection of the incident light illuminating from said defects revealing said cracks and fissures in contrasting dull outlines observable on said surface.
9. The method of claim 8 wherein said inspecting is performed with the unaided eye.

* * * * *